US00PP21508P2

(12) United States Plant Patent
Oudshoorn

(10) Patent No.: US PP21,508 P2
(45) Date of Patent: Nov. 16, 2010

(54) ***SEDUM* PLANT NAME 'MOONLIGHT SERENADE'**

(50) Latin Name: *Hylotelephium spectabile*
Varietal Denomination: Moonlight Serenade

(75) Inventor: Hubertus Gerardus Oudshoorn, Rijpwetering (NL)

(73) Assignee: Future Plants Licentie B.V., Lissenbroek (NL)

( * ) Notice: Subject to any disclaimer, the term of this patent is extended or adjusted under 35 U.S.C. 154(b) by 0 days.

(21) Appl. No.: 12/459,835

(22) Filed: Jul. 8, 2009

(51) Int. Cl.
*A01H 5/00* (2006.01)

(52) U.S. Cl. ..... Plt./479

(58) Field of Classification Search ..... Plt./479
See application file for complete search history.

*Primary Examiner*—June Hwu
(74) *Attorney, Agent, or Firm*—C. A. Whealy

(57) ABSTRACT

A new and distinct cultivar of *Sedum* plant named 'Moonlight Serenade', characterized by its upright and compact plant habit; freely basally branching habit; dense and bushy growth habit; attractive white-colored flowers with greyed purple-colored apices; and good garden performance.

2 Drawing Sheets

Botanical designation: *Hylotelephium spectabile.*
Cultivar denomination: 'MOONLIGHT SERENADE'.

BACKGROUND OF THE INVENTION

The present invention relates to a new and distinct cultivar of *Sedum* plant, botanically known as *Hylotelephium spectabile* and hereinafter referred to by the name 'Moonlight Serenade'.

The new *Sedum* plant is a product of a planned breeding program conducted by the Inventor in Rijpwetering, The Netherlands. The objective of the breeding program is to create new strong and healthy *Sedum* cultivars with numerous attractive flowers.

The new *Sedum* plant originated from a cross-pollination during the summer of 2005 in Rijpwetering, The Netherlands, of *Sedum telephium* 'Xenox', disclosed in U.S. Plant Pat. No. 16,888, as the female, or seed, parent with *Sedum telephium* 'Bronco', disclosed in U.S. Plant Pat. No. 18,085, as the male, or pollen, parent. The new *Sedum* was discovered and selected by the Inventor as a single flowering plant within the progeny of the stated cross-pollination in a controlled greenhouse environment in Rijpwetering, The Netherlands during the summer of 2006.

Asexual reproduction of the new *Sedum* plant by vegetative cuttings in a controlled environment in Rijpwetering, The Netherlands since the summer of 2006, has shown that the unique features of this new *Sedum* plant are stable and reproduced true to type in successive generations.

SUMMARY OF THE INVENTION

Plants of the new *Sedum* have not been observed under all possible environmental conditions. The phenotype may vary somewhat with variations in environment such as temperature and light intensity without, however, any variance in genotype.

The following traits have been repeatedly observed and are determined to be the unique characteristics of 'Moonlight Serenade'.

These characteristics in combination distinguish 'Moonlight Serenade' as a new and distinct cultivar of *Sedum:*

1. Upright and compact plant habit.
2. Freely basally branching habit; dense and bushy growth habit.
3. Attractive white-colored flowers with greyed purple-colored apices.
4. Good garden performance.

Plants of the new *Sedum* differ from plants of the female parent, 'Xenox', in the following characteristics:

1. Plants of the new *Sedum* are more compact than and not as broad as plants of 'Xenox'.
2. Plants of the new *Sedum* have white-colored flowers with greyed purple-colored apices whereas plants of 'Xenox' have orange white to greyed yellow-colored flowers.

Plants of the new *Sedum* differ from plants of the male parent, 'Bronco', in the following characteristics:

1. Plants of the new *Sedum* have smaller leaves than plants of 'Bronco'.
2. Plants of the new *Sedum* have white-colored flowers with greyed purple-colored apices whereas plants of 'Bronco' have yellow green-colored flowers.

Plants of the new *Sedum* can be compared to plants of *Sedum telephium* 'Sunkissed', disclosed in U.S. Plant Pat. No. 16,927. Plants of the new *Sedum* and Sunkissed' differ primarily in flower color as plants of 'Sunkissed' have yellow-colored flowers.

BRIEF DESCRIPTION OF THE PHOTOGRAPHS

The accompanying colored photographs illustrate the overall appearance of the new *Sedum* plant, showing the colors as true as it is reasonably possible to obtain in colored reproductions of this type. Colors in the photographs may differ slightly from the color values cited in the detailed botanical description which accurately describe the colors of the new *Sedum* plant.

The photograph on the first sheet comprises a side perspective view of a typical flowering plant of 'Moonlight Serenade' grown in an outdoor nursery.

The photograph at the top of the second sheet is a close-up view of typical inflorescences of 'Moonlight Serenade'.

The photograph at the bottom of the second sheet is a close-up view of typical leaves and developing inflorescences of 'Moonlight Serenade'.

DETAILED BOTANICAL DESCRIPTION

The aforementioned photographs and following observations, measurements and values describe plants grown in Rijpwetering, The Netherlands, under commercial practice during the late summer in an outdoor nursery with day temperatures ranging from 12° C. to 32° C. and night temperatures ranging from 6° C. to 18° C. Plants used in the photographs and description were two years old. In the following description, color references are made to The Royal Horticultural Society Colour Chart, 2007 Edition, except where general terms of ordinary dictionary significance are used.

Botanical classification: *Hylotelephium spectabile* 'Moonlight Serenade'.

Parentage:

*Female, or seed, parent.*—*Sedum telephium* 'Xenox', disclosed in U.S. Plant Pat. No. 16,888.

*Male, or pollen, parent.*—*Sedum telephium* 'Bronco', disclosed in U.S. Plant Pat. No. 18,085.

Propagation:

*Type.*—By vegetative cuttings.

*Time to initiate roots.*—About 15 to 20 days at 18° C.

*Time to produce a rooted young plant.*—About two months at 16° C. to 22° C.

*Root description.*—Moderately thick and moderately fleshy; white to medium brown in color.

*Rooting habit.*—Moderately freely branching; moderately dense.

Plant description:

*Plant form/habit.*—Herbaceous perennial; upright and compact plant habit; broad inverted triangle; moderately vigorous growth habit; freely basally branching habit with about six basal branches developing per plant; dense and bushy growth habit.

*Plant height.*—About 17.6 cm.

*Plant width* (*spread*).—About 20 cm.

*Lateral branches.*—Length: About 9.6 cm. Diameter: About 5 mm. Internode length: About 3.1 cm. Strength: Strong. Texture: Smooth, glabrous. Color: Close to 187C; the nodes, close to 144C to 144D.

Foliage description:

*Arrangement.*—Opposite, simple; sessile.

*Length.*—About 7.2 cm.

*Width.*—About 5 cm.

*Shape.*—Ovate.

*Apex.*—Bluntly acute to rounded.

*Base.*—Truncate.

*Margin.*—Irregularly and shallowly dentate.

*Texture, upper and lower surfaces.*—Smooth, glabrous; succulent.

*Venation pattern.*—Pinnate.

*Color.*—Developing leaves, upper surface: Close to 137A. Developing leaves, lower surface: Close to 191A. Fully expanded leaves, upper surface: Close to 147A; venation, close to 144B, towards the base, close to N186C. Fully expanded leaves, lower surface: Between 148B to 191A; venation, close to 144A to 144B.

Flower description:

*Flower type/habit.*—Small rotate flowers arranged in terminal compound cymes; flowers face upright to slightly outward; freely flowering habit with about 2,100 flower buds and flowers developing per plant.

*Fragrance.*—None detected.

*Natural flowering season.*—Continuously flowering during August and September in The Netherlands.

*Postproduction longevity.*—Flowers last about two weeks on the plant; flowers persistent.

*Flower buds.*—Height: About 5 mm. Diameter: About 3 mm. Shape: Ovate. Color: Close to 157B; towards the apex, close to 174A to 174B.

*Inflorescence height.*—About 6.3 cm.

*Inflorescence diameter.*—About 7.1 cm.

*Flower diameter.*—About 8 mm.

*Flower depth.*—About 7 mm.

*Petals.*—Quantity per flower: Typically five in a single whorl; petals fused at the base. Length: About 6 mm. Lobe width: About 2 mm. Shape: Ovate. Apex: Acute. Margin: Entire. Texture, upper and lower surfaces: Smooth, glabrous. Color: When opening, upper and lower surfaces: Close to N155C to N155D; towards the apex, slightly lighter than 186D. Fully opened, upper and lower surfaces: Close to N155C to N155D; towards the apex, slightly lighter than 186D.

*Sepals.*—Quantity per flower: Typically five in a single whorl, fused at the base. Length: About 2 mm. Width: About 1 mm. Shape: Narrowly ovate. Apex: Acute. Margin: Entire. Texture, upper and lower surfaces: Smooth, glabrous. Color: When opening, upper and lower surfaces: Close to 146B. Fully opened, upper and lower surfaces: Close to 146B.

*Peduncles.*—Length: About 4.8 cm. Diameter: About 3 mm. Angle: Erect to about 30° from vertical. Strength: Moderately strong. Texture: Smooth, glabrous. Color: Close to 187C.

*Pedicels.*—Length: About 4 mm. Diameter: About 0.7 mm. Angle: Erect to about 40° from vertical. Strength: Moderately strong. Texture: Smooth, glabrous. Color: Close to 146B.

*Reproductive organs.*—Stamens: Quantity per flower: Typically ten. Filament length: About 4 mm. Filament color: Close to 4D. Anther shape: Broadly oblong, flattened. Anther length: About 0.5 mm. Anther color: Close to 35B. Pollen amount: Scarce. Pollen color: Close to 12B. Pistils: Quantity per flower: Five. Pistil length: About 4.5 mm. Stigma shape: Pointed. Stigma color: Close to 22A. Style length: About 4 mm. Style color: Close to 1C to 1D. Ovary color: Close to 1D.

*Seed/fruit.*—Seed and fruit development have not been observed.

Disease/pest resistance: Plants of the new *Sedum* have not been noted to be resistant to pathogens and pests common to *Sedum*.

Garden performance: Plants of the new *Sedum* have been observed to have good garden performance and tolerate rain and wind. Plants of the new *Sedum* tolerate high temperatures of about 35° C. and are winter hardy to USDA Hardiness Zone 5.

It is claimed:

1. A new and distinct *Sedum* plant named 'Moonlight Serenade' as illustrated and described.

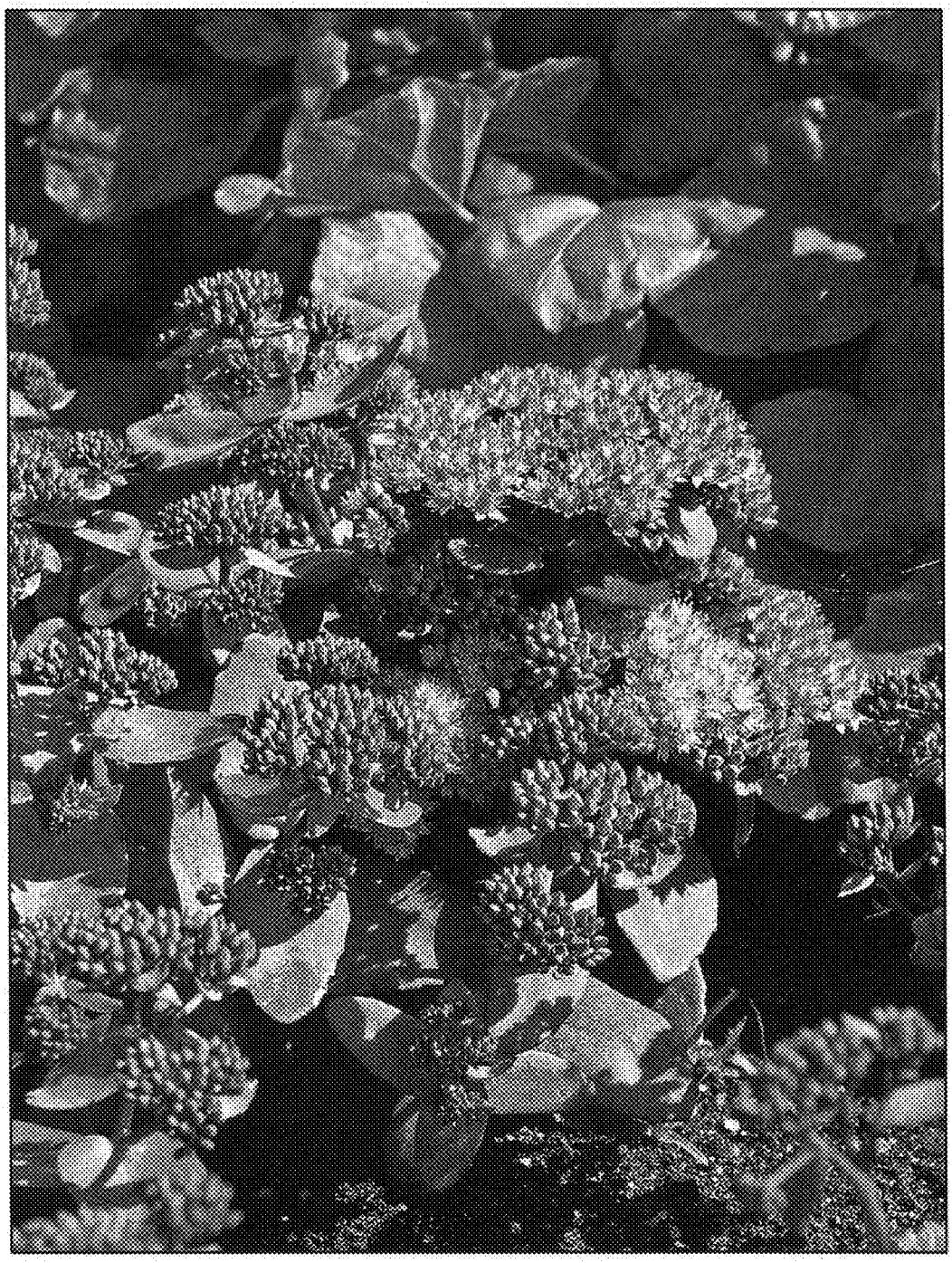

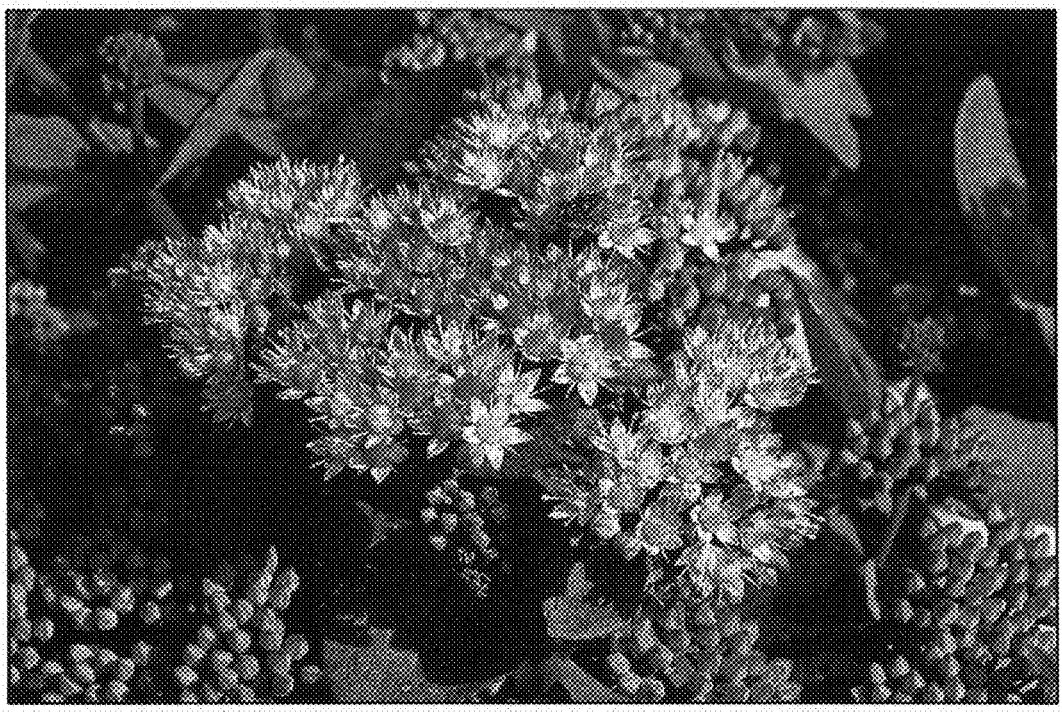
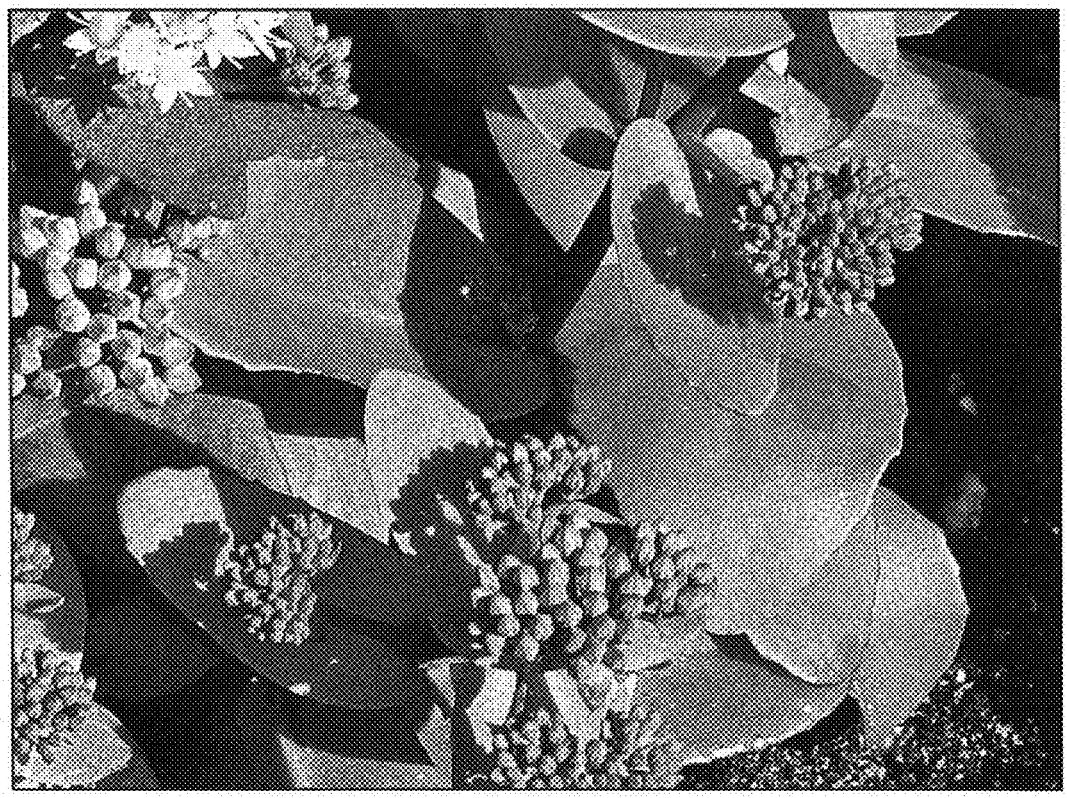

* * * * *